US012779217B2

(12) United States Patent
Giladi et al.

(10) Patent No.: US 12,779,217 B2
(45) Date of Patent: Nov. 3, 2026

(54) INCREASING THE EFFICACY OF TUMOR TREATING FIELDS (TTFIELDS) BY APPLYING THE TTFIELDS AT PEAK INTENSITY LESS THAN HALF THE TIME

(71) Applicant: Novocure GmbH, Root (CH)

(72) Inventors: Moshe Giladi, Haifa (IL); Eyal Dor-On, Haifa (IL); Einav Zeevi, Haifa (IL); Rotem Engelman, Haifa (IL)

(73) Assignee: Novocure GmbH, Baar (CH)

( * ) Notice: Subject to any disclaimer, the term of this patent is extended or adjusted under 35 U.S.C. 154(b) by 491 days.

(21) Appl. No.: 17/533,604

(22) Filed: Nov. 23, 2021

(65) Prior Publication Data

US 2022/0161028 A1 May 26, 2022

Related U.S. Application Data

(60) Provisional application No. 63/118,411, filed on Nov. 25, 2020.

(51) Int. Cl.
*A61N 1/36* (2006.01)

(52) U.S. Cl.
CPC ..... *A61N 1/36002* (2017.08); *A61N 1/36171* (2013.01)

(58) Field of Classification Search
CPC .............. A61N 1/36002; A61N 1/3603; A61N 1/36146; A61N 1/36167; A61N 1/36175
See application file for complete search history.

(56) References Cited

U.S. PATENT DOCUMENTS

| | | | |
|---|---|---|---|
| 5,233,987 | A | 8/1993 | Fabian et al. |
| 6,868,289 | B2 | 3/2005 | Palti |
| 7,016,725 | B2 | 3/2006 | Palti |
| 7,089,054 | B2 | 8/2006 | Palti |
| 7,136,699 | B2 | 11/2006 | Palti |
| 7,333,852 | B2 | 2/2008 | Palti |
| 7,467,011 | B2 | 12/2008 | Palti |

(Continued)

FOREIGN PATENT DOCUMENTS

| | | | |
|---|---|---|---|
| KR | 20160134469 | A | 11/2016 |
| WO | 2019084011 | A1 | 5/2019 |

(Continued)

OTHER PUBLICATIONS

International Search Report and Written Opinion issued in application No. PCT/IB2021/060876 dated Feb. 23, 2022.

*Primary Examiner* — David Hamaoui
*Assistant Examiner* — Jessandra F Hough
(74) *Attorney, Agent, or Firm* — Potomac Law Group, PLLC

(57) ABSTRACT

An alternating electric field may be applied to a target region in a living body or to cells in vitro. The alternating electric field is applied during a first interval of time that is at least 1 hour long. The first interval of time includes a plurality of (e.g., 10) non-overlapping sub-intervals of time per hour. In each of the sub-intervals of time, (a) the alternating electric field has a frequency between 50 kHz and 1 MHz (e.g., 50-500 kHz, or 100-300 kHz), (b) the alternating electric field has a respective peak intensity of at least 0.1 V/cm in at least a portion of the target region, and (c) the alternating electric field remains at the respective peak intensity less than 75% the time (e.g., 25% or 33% of the time).

23 Claims, 8 Drawing Sheets

(56) References Cited

U.S. PATENT DOCUMENTS 7,519,420 B2 4/2009 Palti
7,565,205 B2 7/2009 Palti
7,565,206 B2 7/2009 Palti
7,599,745 B2 10/2009 Palti
7,599,746 B2 10/2009 Palti
7,706,890 B2 4/2010 Palti
7,715,921 B2 5/2010 Palti
7,805,201 B2 9/2010 Palti
7,890,183 B2 2/2011 Palti et al.
7,912,540 B2 3/2011 Palti
7,917,227 B2 3/2011 Palti
8,019,414 B2 9/2011 Palti
8,027,738 B2 9/2011 Palti
8,170,684 B2 5/2012 Palti
8,175,698 B2 5/2012 Palti et al.
8,229,555 B2 7/2012 Palti
RE43,618 E 8/2012 Palti
8,244,345 B2 8/2012 Palti
8,406,870 B2 3/2013 Palti
8,447,395 B2 5/2013 Palti et al.
8,447,396 B2 5/2013 Palti et al.
8,465,533 B2 6/2013 Palti
8,706,261 B2 4/2014 Palti
8,715,203 B2 5/2014 Palti
8,718,756 B2 5/2014 Palti
8,764,675 B2 7/2014 Palti
9,023,090 B2 5/2015 Palti
9,023,091 B2 5/2015 Palti
9,039,674 B2 5/2015 Palti et al.
9,056,203 B2 6/2015 Palti et al.
9,440,068 B2 9/2016 Palti et al.
9,655,669 B2 5/2017 Palti et al.
9,750,934 B2 9/2017 Palti et al.
9,910,453 B2 3/2018 Wasserman et al.
10,188,851 B2 1/2019 Wenger et al.
10,441,776 B2 10/2019 Kirson et al.
11,191,956 B2 12/2021 Giladi et al.
2005/0222646 A1* 10/2005 Kroll ...................... A61N 1/326 607/72
2006/0167499 A1 7/2006 Palti
2007/0097593 A1* 5/2007 Armstrong ......... A61N 1/36139 361/232
2007/0225766 A1* 9/2007 Palti ................... A61N 1/36002 607/2
2007/0239213 A1 10/2007 Palti
2009/0076366 A1 3/2009 Palti
2009/0182394 A1 7/2009 Bachinski
2012/0283726 A1 11/2012 Palti
2014/0330268 A1 11/2014 Palti et al.
2015/0119952 A1* 4/2015 Sharma ................ A61N 1/3606 607/40
2017/0120041 A1 5/2017 Wenger et al.
2017/0215939 A1 8/2017 Palti et al.
2017/0281934 A1 10/2017 Giladi et al.
2018/0001075 A1 1/2018 Kirson et al.
2018/0008708 A1 1/2018 Giladi et al.
2018/0050200 A1 2/2018 Wasserman et al.
2018/0104486 A1 4/2018 Yoon et al.
2018/0160933 A1 6/2018 Urman et al.
2018/0202991 A1 7/2018 Giladi et al.
2019/0117956 A1 4/2019 Wenger et al.
2019/0117963 A1 4/2019 Travers et al.
2019/0117969 A1* 4/2019 Schmidt .............. A61N 1/0424
2019/0307781 A1 10/2019 Krex et al.
2019/0308016 A1 10/2019 Wenger et al.
2020/0001069 A1 1/2020 Kirson et al.
2020/0009376 A1 1/2020 Chang et al.
2020/0009377 A1 1/2020 Chang et al.
2020/0016067 A1 1/2020 Gotlib et al.
2020/0023179 A1 1/2020 Bomzon et al.
2020/0061360 A1 2/2020 Hagemann et al.
2020/0061361 A1 2/2020 Hagemann et al.
2020/0069937 A1 3/2020 Naveh et al.
2020/0078582 A1 3/2020 Alon et al.
2020/0108031 A1 4/2020 Borst et al.
2020/0121728 A1 4/2020 Wardak et al.
2020/0129761 A1 4/2020 Bomzon et al.
2020/0146586 A1 5/2020 Naveh et al.
2020/0155835 A1 5/2020 Wasserman et al.
2020/0171297 A1 6/2020 Kirson et al.
2020/0179512 A1 6/2020 Giladi et al.
2020/0219261 A1 7/2020 Shamir et al.
2020/0269041 A1 8/2020 Zeevi et al.
2020/0368525 A1 11/2020 Maag et al.
2021/0031031 A1 2/2021 Wasserman et al.
2021/0038584 A1 2/2021 Voloshin-Sela
2021/0060334 A1 3/2021 Avraham et al.
2021/0069503 A1 3/2021 Tran et al.
2021/0187277 A1 6/2021 Wasserman et al.
2021/0196348 A1 7/2021 Wasserman
2021/0199640 A1 7/2021 Patel et al.
2021/0203250 A1 7/2021 Wasserman
2021/0228874 A1* 7/2021 Scheiner ............ A61N 1/36192
2021/0268247 A1 9/2021 Story et al.
2021/0299440 A1 9/2021 Deslauriers et al.
2021/0308446 A1 10/2021 Alon et al.
2021/0330950 A1 10/2021 Hagemann et al.
2021/0346694 A1 11/2021 Wasserman et al.
2021/0379362 A1 12/2021 Smith et al.
2021/0408383 A1 12/2021 Kalra et al.

FOREIGN PATENT DOCUMENTS

WO 2019155407 A2 8/2019
WO 2021137085 A2 7/2021

* cited by examiner

INCREASING THE EFFICACY OF TUMOR TREATING FIELDS (TTFIELDS) BY APPLYING THE TTFIELDS AT PEAK INTENSITY LESS THAN HALF THE TIME

CROSS REFERENCE TO RELATED APPLICATIONS

This application claims the benefit of U.S. Provisional Application 63/118,411 filed Nov. 25, 2020, which is incorporated herein by reference in its entirety.

BACKGROUND

Tumor Treating Fields, or TTFields, are alternating electric fields within the intermediate frequency range (e.g., 100-500 kHz) that inhibit cancer cell growth. This non-invasive treatment targets solid tumors and is described in U.S. Pat. No. 7,565,205, which is incorporated herein by reference in its entirety. 200 kHz TTFields are FDA approved for the treatment of glioblastoma (GBM), and may be delivered, for example, via the prior art Optune™ system. Optune™ includes a field generator and two pairs of transducer arrays (i.e., electrode arrays) that are placed on the patient's shaved head. One pair of arrays (L/R) is positioned to the left and right of the tumor, and the other pair of arrays (A/P) is positioned anterior and posterior to the tumor. In the preclinical setting, TTFields can be applied in vitro using, for example, the prior art Inovitro™ TTFields lab bench system. In both Optune™ and Inovitro™, the field generator (a) applies an AC voltage between the L/R transducer arrays (or electrodes) for 1 second; then (b) applies an AC voltage between the A/P transducer arrays (or electrodes) for 1 second; then repeats that two-step sequence (a) and (b) for the duration of the treatment.

FIG. 1 is a schematic representation of the AC output amplitudes of the L/R channel and the A/P channel in Optune™. Notably, when the signal to either the A/P or L/R transducer arrays is turned on during any given one-second interval, the amplitude of the AC voltage does not jump immediately to its peak value. Instead, the amplitude of the AC voltage ramps up from zero to its peak over the course of a 50 ms window. Similarly, when the signal is turned off during any given one-second interval, the amplitude of the AC voltage ramps down from its peak to zero over the course of a 50 ms window. Because each 1 second interval includes a 50 ms ramp-up window and a 50 ms ramp-down window, the AC voltage remains at its peak value for 900 ms out of each 1 second interval.

Details A and B in FIG. 1 are schematic representations of the instantaneous output voltage during the ramp-up and ramp-down windows. Note that although each of these details depicts only 9 cycles in the 50 ms ramp-up and ramp-down windows, each of those windows will really contain about 10,000 cycles (assuming 200 kHz TTFields are being delivered).

SUMMARY OF THE INVENTION

One aspect of the invention is directed to a first method of inhibiting growth of cancer cells. The first method comprises applying an alternating electric field to the cancer cells during a first interval of time that is at least 1 hour long, wherein the first interval of time includes a plurality of non-overlapping sub-intervals of time per hour. In each of the sub-intervals of time, (a) the alternating electric field has a frequency between 50 and 500 kHz, (b) the alternating electric field has a respective peak intensity of at least 1 V/cm in at least a portion of the cancer cells, and (c) the alternating electric field remains at the respective peak intensity less than half the time.

In some instances of the first method, within each of the sub-intervals of time, the alternating electric field ramps up to the respective peak intensity during an interval of time that precedes the respective peak intensity. Optionally, in these instances, within each of the sub-intervals of time, the alternating electric field ramps up linearly to the respective peak intensity during the interval of time that precedes the respective peak intensity.

In some instances of the first method, within each of the sub-intervals of time, the alternating electric field remains off at least half the time.

In some instances of the first method, within each of the sub-intervals of time, the alternating electric field remains at the respective peak intensity less than 25% of the time. Optionally, in these instances, within each of the sub-intervals of time, the alternating electric field remains off at least 75% of the time. Optionally, in these instances, within each of the sub-intervals of time, the alternating electric field remains within 90% of the respective peak intensity at least 5% of the time.

In some instances of the first method, within each of the sub-intervals of time, the alternating electric field has a respective peak intensity of 1-10 V/cm in at least a portion of the cancer cells.

In some instances of the first method, the first interval of time includes at least 10 non-overlapping sub-intervals of time per hour. In some instances of the first method, the alternating electric field is applied to the cancer cells in a first direction during a first subset of the sub-intervals, and the alternating electric field is applied to the cancer cells in a second direction during a second subset of the sub-intervals, wherein the second direction is offset from the first direction by at least 45°.

In some instances of the first method, within each of the sub-intervals of time, the alternating electric field remains at the respective peak intensity less than 25% of the time; the first interval of time includes at least 10 non-overlapping sub-intervals of time per hour; the alternating electric field is applied to the cancer cells in a first direction during a first subset of the sub-intervals; and the alternating electric field is applied to the cancer cells in a second direction during a second subset of the sub-intervals, wherein the second direction is offset from the first direction by at least 45°.

Another aspect of the invention is directed to a first apparatus that comprises a signal generator and a controller. The signal generator has at least one control input, and the signal generator is configured to generate a first AC output at a frequency between 50 and 500 kHz. The first AC output has an amplitude that depends on a state of the at least one control input. The controller is configured to send a first set of control signals to the at least one control input during each of a plurality of non-overlapping first sub-intervals of time per hour, and the first set of control signals is configured to cause the first AC output to operate at a respective peak amplitude for less than half of each respective first sub-interval of time.

In some embodiments of the first apparatus, the first set of control signals is configured so that during each of the first sub-intervals of time, the first set of control signals will cause the first AC output to ramp up to the respective peak amplitude during an interval of time that precedes the respective peak amplitude. Optionally, in these embodiments, the first set of control signals is configured so that during each of the first sub-intervals of time, the first set of control signals will cause the first AC output to ramp up linearly to the respective peak amplitude during the interval of time that precedes the respective peak amplitude.

In some embodiments of the first apparatus, the first set of control signals is configured so that during each of the first sub-intervals of time, the first set of control signals will cause the first AC output to remain off at least half the time.

In some embodiments of the first apparatus, the first set of control signals is configured so that during each of the first sub-intervals of time, the first set of control signals will cause the first AC output to remain at the respective peak amplitude less than 25% of the time.

Optionally, in the embodiments of the previous paragraph, the first set of control signals is configured so that during each of the first sub-intervals of time, the first set of control signals will cause the first AC output to remain off at least 75% of the time.

Optionally, in the embodiments of the previous paragraph, the first set of control signals is configured so that during each of the first sub-intervals of time, the first set of control signals will cause the first AC output to remain within 90% of the respective peak amplitude at least 5% of the time.

In some embodiments of the first apparatus, the first set of control signals is configured so that during each of the first sub-intervals of time, the first set of control signals will cause the first AC output to have a respective peak amplitude of at least 50 V.

In some embodiments of the first apparatus, the controller is configured to send the first set of control signals to the at least one control input during each of at least 10 non-overlapping first sub-intervals of time per hour.

In some embodiments of the first apparatus, the signal generator is further configured to generate a second AC output at a frequency between 50 and 500 kHz; the second AC output has an amplitude that depends on a state of the at least one control input; and the controller is further configured to send a second set of control signals to the at least one control input during each of a plurality of non-overlapping second sub-intervals of time per hour, wherein the second set of control signals is configured to cause the second AC output to operate at a respective peak amplitude for less than half of each second respective sub-interval of time, and wherein each of the second sub-intervals of time follows a respective one of the first sub-intervals of time.

Optionally, in the embodiments of the previous paragraph, the first set of control signals is configured so that during each of the first sub-intervals of time, the first set of control signals will cause the first AC output to remain at the respective peak amplitude less than 25% of the time, and the second set of control signals is configured so that during each of the second sub-intervals of time, the second set of control signals will cause the second AC output to remain at the respective peak amplitude less than 25% of the time.

Optionally, in the embodiments of the previous paragraph, the controller is configured to send the first set of control signals to the at least one control input during each of at least 10 non-overlapping first sub-intervals of time per hour, and the controller is configured to send the second set of control signals to the at least one control input during each of at least 10 non-overlapping second sub-intervals of time per hour.

Optionally, in the embodiments of the previous paragraph, the first set of control signals is configured so that during each of the first sub-intervals of time, the first set of control signals will cause the first AC output to have a respective peak amplitude of at least 50 V, and the second set of control signals is configured so that during each of the second sub-intervals of time, the second set of control signals will cause the second AC output to have a respective peak amplitude of at least 50 V.

Another aspect of the invention is directed to a third method of applying an electric field to a target region in a living body. This method comprises applying an alternating electric field to the target region during a first interval of time that is at least 1 hour long, wherein the first interval of time includes a plurality of non-overlapping sub-intervals of time per hour. In each of the sub-intervals of time, (a) the alternating electric field has a frequency between 50 kHz and 1 MHz, (b) the alternating electric field has a respective peak intensity of at least 0.1 V/cm in at least a portion of the target region, and (c) the alternating electric field remains at the respective peak intensity less than 75% the time.

In some instances of the third method, within each of the sub-intervals of time, the alternating electric field ramps up to the respective peak intensity during an interval of time that precedes the respective peak intensity. Optionally, in these instances, within each of the sub-intervals of time, the alternating electric field ramps up linearly to the respective peak intensity during the interval of time that precedes the respective peak intensity.

In some instances of the third method, within each of the sub-intervals of time, the alternating electric field remains off at least 75% of the time.

In some instances of the third method, within each of the sub-intervals of time, the alternating electric field remains at the respective peak intensity less than 50%, for example less than 25% of the time. Optionally, in these instances, within each of the sub-intervals of time, the alternating electric field remains off at least 50% of the time. Optionally, in these instances, within each of the sub-intervals of time, the alternating electric field remains within 90% of the respective peak intensity at least 5% of the time.

In some instances of the third method, within each of the sub-intervals of time, the alternating electric field has a respective peak intensity of 1-10 V/cm in at least a portion of the target region.

In some instances of the third method, the first interval of time includes at least 3 or at least 10 non-overlapping sub-intervals of time per hour. In some instances of the third method, the alternating electric field is applied to the target region in a first direction during a first subset of the sub-intervals, and the alternating electric field is applied to the target region in a second direction during a second subset of the sub-intervals, wherein the second direction is offset from the first direction by at least 45°.

In some instances of the third method, within each of the sub-intervals of time, the alternating electric field remains at the respective peak intensity less than half the time; the first interval of time includes at least 10 non-overlapping sub-intervals of time per hour; the alternating electric field is applied to the target region in a first direction during a first subset of the sub-intervals; and the alternating electric field is applied to the target region in a second direction during a second subset of the sub-intervals, wherein the second direction is offset from the first direction by at least 45°.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Persons skilled in the relevant arts previously assumed that TTFields would be most effective when the TTFields are applied at their peak intensity for as much time as possible. But when experiments were performed to see what would happen when the ramp-up and ramp-down windows were extended with respect to the prior art, surprising results were observed. More specifically, the data reveals that when the ramp-up and ramp-down windows were extended from the 50 ms duration used in the prior art to 350 ms each (which means that the AC voltage would only be operating at its peak value for 300 ms out of each 1 second interval), the cytotoxicity (i.e., the killing power) of the TTFields actually increased. And when the ramp-up and ramp-down windows were extended to 400 ms each (which means that the AC voltage would only be operating at its peak value for 200 ms out of each 1 second interval), the cytotoxicity of the TTFields increased even further.

Figure 2:
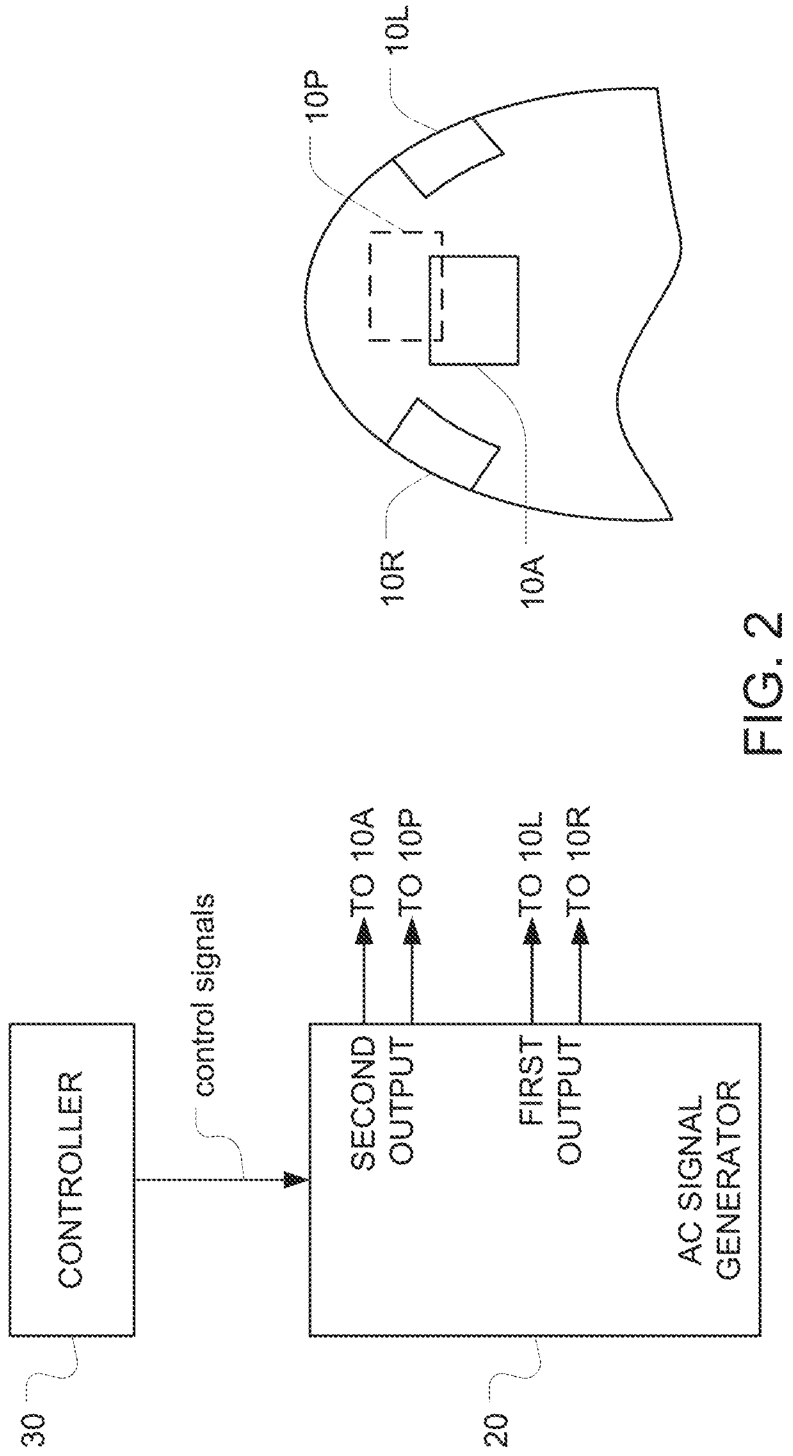
FIG. 2 is a block diagram of a system for driving a set of transducer arrays with AC voltage signals in which the ramp-up and ramp-down times of the AC outputs can be controlled.

FIG. 2 is a block diagram of a system for driving a set of transducer arrays with AC voltage signals in which the ramp-up and ramp-down times of the AC outputs can be controlled. The system includes an AC signal generator 20 that is designed to generate first and second AC outputs at a frequency between 50 and 500 kHz. When the system is used to apply TTFields to a person's body (as shown in FIG. 2), the first AC output is applied across a first pair of electrodes 10L and 10R that are positioned to the left and right of the tumor; and the second AC output is applied across a second pair of electrodes 10A and 10P that are positioned anterior and posterior to a tumor. The AC signal generator 20 could also be used to apply TTFields to an in vitro culture (not shown) by applying the first AC output to electrodes positioned on the left and right walls of an Inovitro™ dish and applying the second AC output to electrodes positioned on the front and back walls of the Inovitro™ dish. In either case, the voltages generated by the AC signal generator 20 should be sufficient to induce an electric field of at least 1 V/cm in at least a portion of the cancer cells. In some embodiments, the voltages generated by the AC signal generator 20 should be sufficient to induce an electric field of between 1 V/cm and 10 V/cm in at least a portion of the cancer cells.

As in the prior art Optune™ and Inovitro™ systems, (a) the first AC output is applied to the L/R electrodes for a 1 second sub-interval of time; (b) the second AC output is applied to the A/P electrodes for a 1 second sub-interval of time; and the two-step sequence (a) and (b) is repeated for the duration of the treatment. But in contrast to Optune™, the ramp-up and ramp-down times were not set to 50 ms. Instead, the AC signal generator 20 is configured to generate first and second AC outputs such that the first and second AC outputs have amplitudes that depend on a state of at least one control input.

A controller 30 continuously sends control signals to the at least one control input during each 1 second sub-interval, and these control signals are configured to cause the first and second AC outputs to operate at their respective peak amplitudes for less than half of each respective 1 second sub-interval of time, and to generate the amplitude profiles described herein. When these waveforms are applied to the electrodes 10, the alternating electric fields that are applied to the cancer cells will remain at their respective peak intensity less than half the time. Note that although FIG. 2 depicts the controller 30 and the AC signal generator 20 as two distinct blocks, those two blocks may be integrated into a single hardware device.

The details of the construction of the controller 30 and the nature of the control signals will depend on the design of the AC signal generator 20. In one example, the design of the AC signal generator 20 is similar to the AC signal generator described in U.S. Pat. No. 9,910,453, which is incorporated herein by reference in its entirety. This particular AC signal generator has two output channels (i.e., a first channel for L/R and a second channel for A/P). The instantaneous AC output voltage on either channel depends on the instantaneous output voltage of a DC-DC converter, and the output voltage of that DC-DC converter is controlled by writing a control word to a digital-to-analog converter (DAC). This AC signal generator can therefore be used to ramp the AC output voltage up from zero to a desired level in 50 ms by updating the control word once per ms during the first 50 ms of any given 1 second sub-interval; and to ramp the AC output voltage back down to zero by updating the control word once per ms during the last 50 ms of any given 1 second sub-interval.

Figure 3:
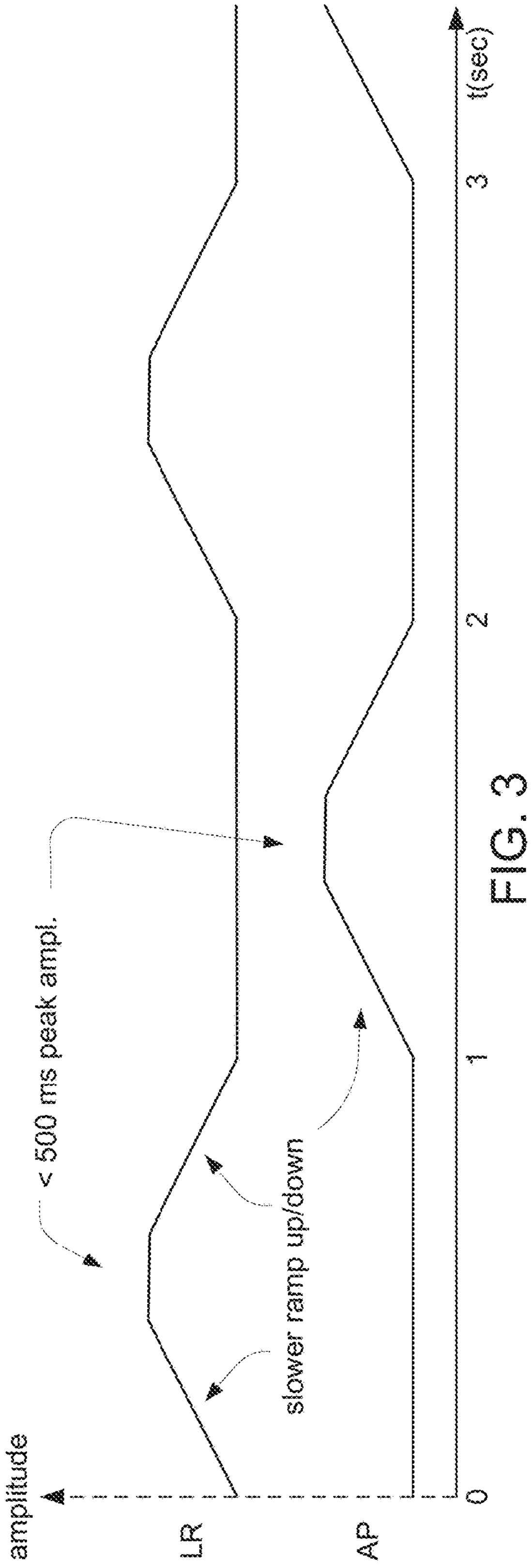
FIG. 3 depicts the AC output amplitudes of the L/R channel and the A/P channel when the ramp-up and ramp-down at times are slowed down.

This very same AC signal generator can be modified to ramp the AC output voltage up and down at faster or slower rates by adjusting the rate at which the control words are written to the DAC. For example, the AC output voltage can be ramped up linearly from zero to a desired level in 400 ms by updating the control word once every 8 ms during the first 400 ms of any given 1 second sub-interval; and to ramp the AC output voltage back down linearly to zero by updating the control word once every 8 ms during the last 400 ms of any given 1 second sub-interval. FIG. 3 depicts the AC output amplitudes of the L/R channel and the A/P channel in this situation. In this example, because a total of 800 ms are used for ramping up and down, the output will only remain at its peak amplitude for 200 ms out of any given 1 second sub-interval.

Figure 4:
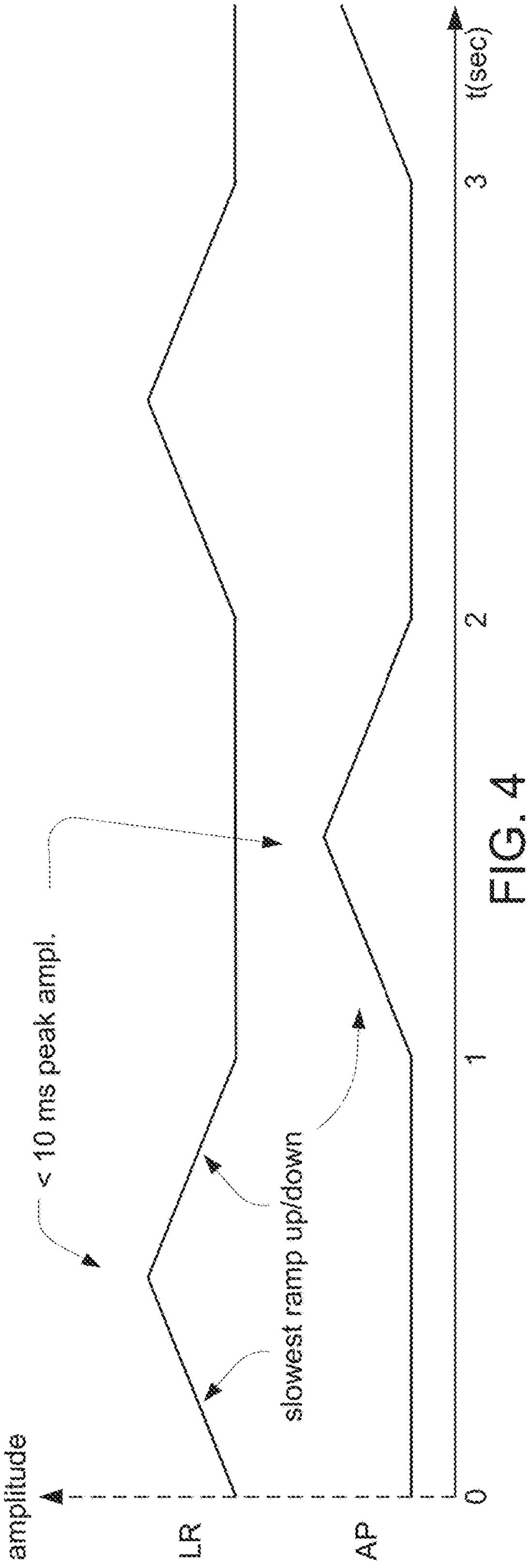
FIG. 4 depicts the AC output amplitudes of the L/R channel and the A/P channel when the ramp-up and ramp-down at times are slowed down even further.

FIG. 4 depicts the AC output amplitudes of the L/R channel and the A/P channel when the ramp-up and ramp-down at times are slowed down even further. More specifically, the AC output voltage is ramped up linearly from zero to a desired level in 500 ms e.g., by updating the control word once every 10 ms during the first 500 ms of any given 1 second sub-interval; and ramped back down linearly to zero e.g., by updating the control word once every 10 ms during the last 500 ms of any given 1 second sub-interval. In this example, because a total of 1000 ms are used for ramping up and down, the output will remain at its peak amplitude for less than 1 ms out of any given 1 second sub-interval.

Note that for any given channel (i.e., the L/R channel or the A/P channel) each sub-interval of time during which the AC output voltage ramps up to its peak, remains at its peak, and ramps down from its peak does not overlap with the next sub-interval of time during which the AC output voltage ramps up to its peak, remains at its peak, and ramps down from its peak. For example, in FIGS. 3 and 4, the sub-interval of time between t=0 and t=1 does not overlap with the sub-interval of time between t=2 and t=3. Similarly, the sub-interval of time between t=1 and t=2 does not overlap with the sub-interval of time between t=3 and t=4.

Returning to FIG. 2, the controller 30 controls the AC signal generator 20 by writing an appropriate sequence of control words to the DAC within the AC signal generator 20 at appropriate times within each 1 second sub-interval, in order to cause the AC signal generator 20 to generate the desired output waveforms.

A wide variety of alternative designs for the AC signal generator 20 and the controller 30 can be substituted for the example provided above, as long as the controller 30 has the ability to control the AC signal generator 20. For example, if the AC signal generator is designed to respond to an analog control signal, the controller 30 must generate whatever sequence of analog control signals is needed to cause the AC signal generator 20 to output the desired waveforms. In this situation, the controller 30 could be implemented using a microprocessor or microcontroller that is programmed to write appropriate control words to a digital-to-analog converter, the output of which generates the analog control signals that causes the AC signal generator 20 to generate the desired waveforms. Alternatively, the controller 30 could be implemented using an analog circuit that automatically generates the appropriate sequence of control signals (which are then applied to the control input of the AC signal generator).

Figure 5:
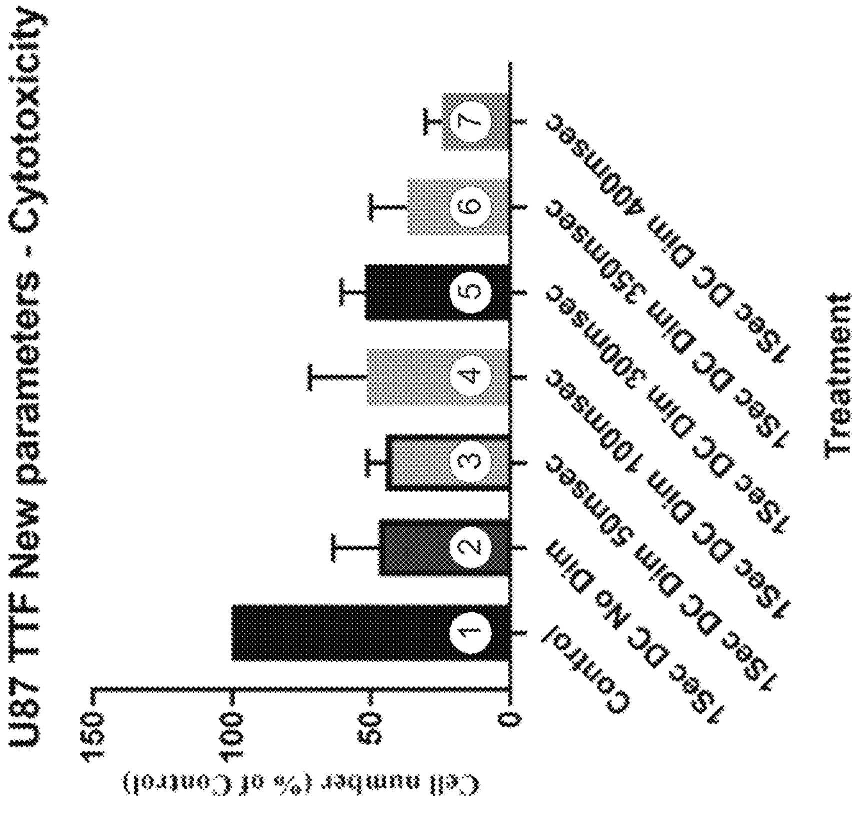
FIG. 5 depicts the results of experiments that were performed to determine how changing the ramp-up and ramp-down times effects cytotoxicity in U87 cells in vitro.

FIG. 5 depicts the results of experiments that were performed to determine how changing the ramp-up and ramp-down times effects cytotoxicity in U87 cells in vitro. The data was obtained using an Inovitro™ system that was modified to provide control over the ramp-up and ramp-down times. (Note that the ramp-up and ramp-down times are referred to in the figures as “dimming” or “dim” times.) Bar #1 represents the control, which was not treated with TTFields. Bar #2 represents the cytotoxicity results when the AC voltage jumped immediately from zero to the peak at the start of each 1 second sub-interval, and jumped immediately from the peak to zero at the end of each 1 second sub-interval. Bar #3 represents the cytotoxicity results when the AC voltage ramped up from zero to the peak in the first 50 ms of each 1 second sub-interval, and ramped down from the peak to zero in the last 50 ms of each 1 second sub-interval. This means that the AC voltage remained at its peak value for 900 ms in each 1 second sub-interval.

Bar #4 represents the cytotoxicity results when the AC voltage ramped up from zero to the peak in the first 100 ms of each 1 second sub-interval, and ramped down from the peak to zero in the last 100 ms of each 1 second sub-interval. This means that the AC voltage remained at its peak value for 800 ms in each 1 second sub-interval. Bar #5 represents the cytotoxicity results when the AC voltage ramped up from zero to the peak in the first 300 ms of each 1 second sub-interval, and ramped down from the peak to zero in the last 300 ms of each 1 second sub-interval. This means that the AC voltage remained at its peak value for 400 ms in each 1 second sub-interval.

Bar #6 represents the cytotoxicity results when the AC voltage ramped up from zero to the peak in the first 350 ms of each 1 second sub-interval, and ramped down from the peak to zero in the last 350 ms of each 1 second sub-interval. This means that the AC voltage remained at its peak value for 300 ms in each 1 second sub-interval. Notably, the cytotoxicity results under these circumstances were better than when 50 ms ramp times were used (see bar #3). Bar #7 represents the cytotoxicity results when the AC voltage ramped up from zero to the peak in the first 400 ms of each 1 second sub-interval, and ramped down from the peak to zero in the last 400 ms of each 1 second sub-interval. This means that the AC voltage remained at its peak value for 200 ms in each 1 second sub-interval. Here again, the cytotoxicity results were better than when 50 ms ramp times were used.

Note that for bars #2-7, (a) the first AC output was applied to the L/R electrodes for 1 second; (b) the second AC output was applied to the A/P electrodes for 1 second; and the two-step sequence (a) and (b) was repeated for the duration of the 120 hour experiment.

Figure 1:
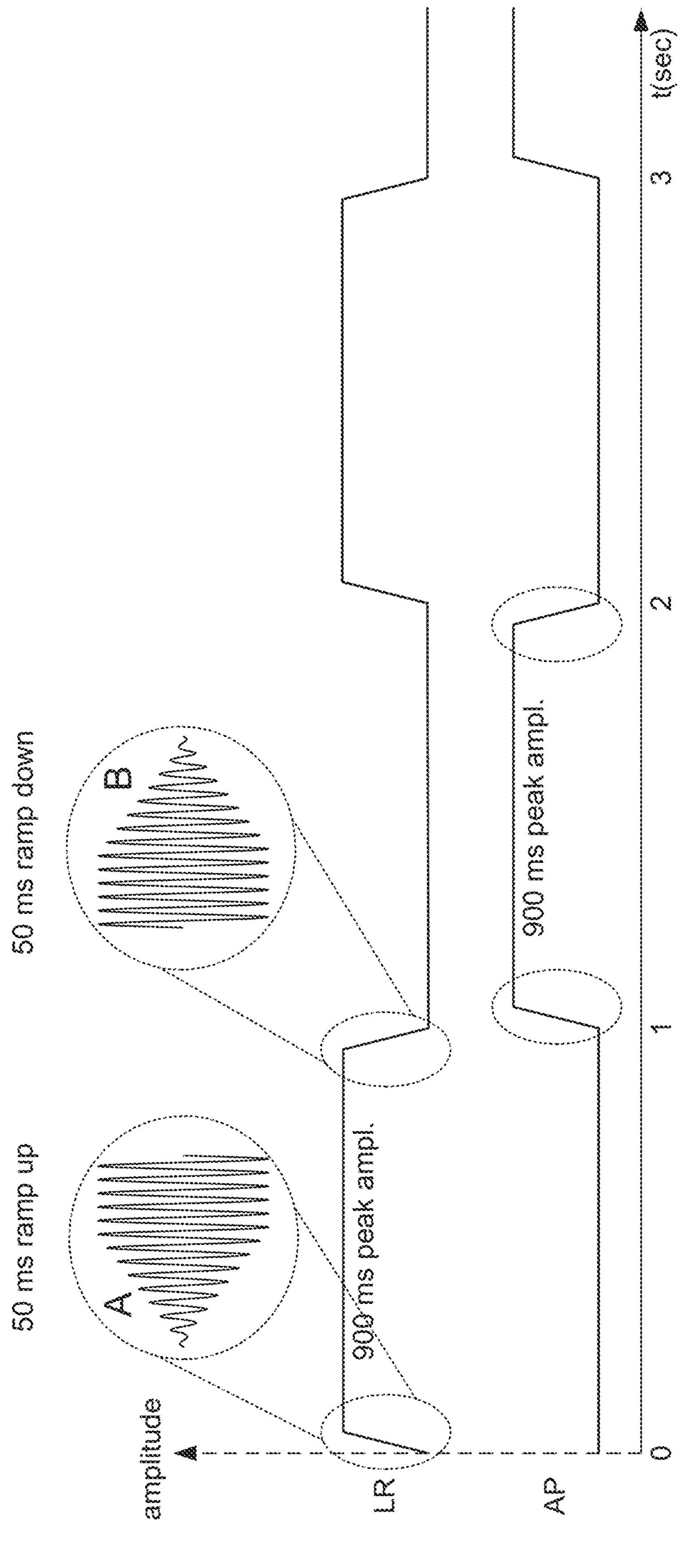
PRIOR ART FIG. 1
FIG. 1 is a schematic representation of the AC output amplitudes of the L/R channel and the A/P channel in the prior art Optune™ system.

One might wonder how a system that only applies TTFields at peak intensity less than 50% of the time (e.g., 20% of the time as depicted in FIG. 3) can possibly outperform a system that applies TTFields at peak intensity 90% of the time (e.g., as depicted in FIG. 1).

It turns out that both Optune™ and Inovitro™ include feedback loops that automatically control the amplitude of the AC voltages that are applied to the electrodes in order to prevent overheating. More specifically, Inovitro™ will automatically adjust the amplitude of the AC voltages applied to the electrodes to keep the sample dishes at 37° C. And Optune™ will automatically adjust the amplitude of the AC voltages applied to the electrodes to the highest level possible that does not cause the electrodes to overheat. Because these feedback loops are in place, when the AC voltages are ramped up and down more slowly (e.g., as depicted in FIGS. 3 and 4), the system will automatically set the AC signal generator's 20 peak output voltages to higher levels (as compared to a system that spends a higher percentage of time operating at its peak output voltage).

Figure 6:
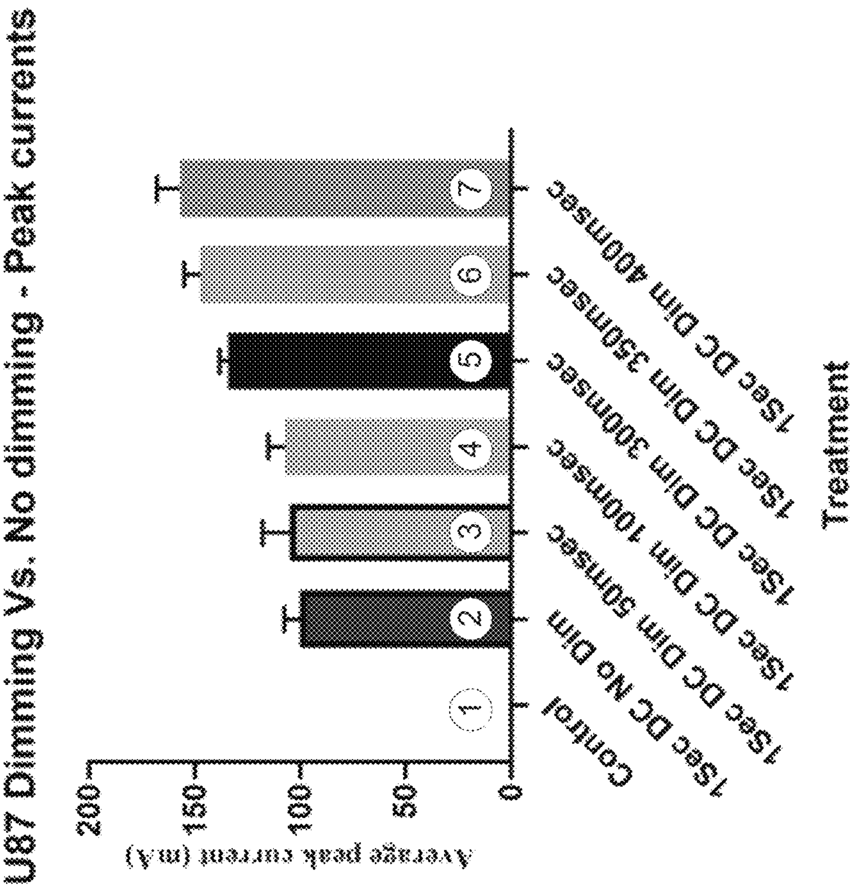
FIG. 6 depicts the peak current that was applied during the FIG. 5 experiments.

FIG. 6 depicts the peak current that was applied by the Inovitro™ system that was modified to provide adjustable ramp-up and ramp-down rates during the FIG. 5 experiments. Each of the numbered bars in FIG. 6 corresponds to a respective numbered bar in FIG. 5. The data in FIG. 6 reveals that the less time the system spends at its peak voltage (and current) during each 1 second sub-interval, the higher the peak current will be during that 1 second sub-interval (after the system has automatically set the peak voltage to a level that does not cause overheating, as described in the previous paragraph). For example, bar #3 in FIG. 6 indicates that the peak current was about 100 mA when the AC voltage (and current) remained at its peak value for 900 ms in each 1 second sub-interval; while bar #7 indicates that the peak current was roughly 50% higher when the AC voltage (and current) remained at its peak value for 200 ms in each 1 second sub-interval. And because voltage is proportional to current, we can assume that the peak output voltages associated with bar #7 were also about 50% higher than the peak output voltages associated with bar #3.

This data shows that TTFields with higher peak intensities (which correspond to the measured higher peak currents) that are applied for a smaller percentage (e.g., 20%, 30%, or less than 50%) of time in each 1 second sub-interval are more cytotoxic than TTFields with lower peak intensities that are applied for a larger percentage (e.g., 100%, 90%, or at least 50%) of time in each 1 second sub-interval.

In the examples described above, the controller 30 causes the AC signal generator 20 to generate first and second outputs with amplitudes as depicted in FIGS. 3 and 4. Although those two examples have peaks with different durations (200 ms in FIG. 3, and less than 1 ms in FIG. 4), in both examples the ramping up begins at the very start of each 1 second sub-interval, and the ramping down continues until the very end of each 1 second sub-interval. But in alternative embodiments, the ramping up can begin at a later time within each 1 second sub-interval and can end at an earlier time within each 1 second sub-interval.

Figure 7:
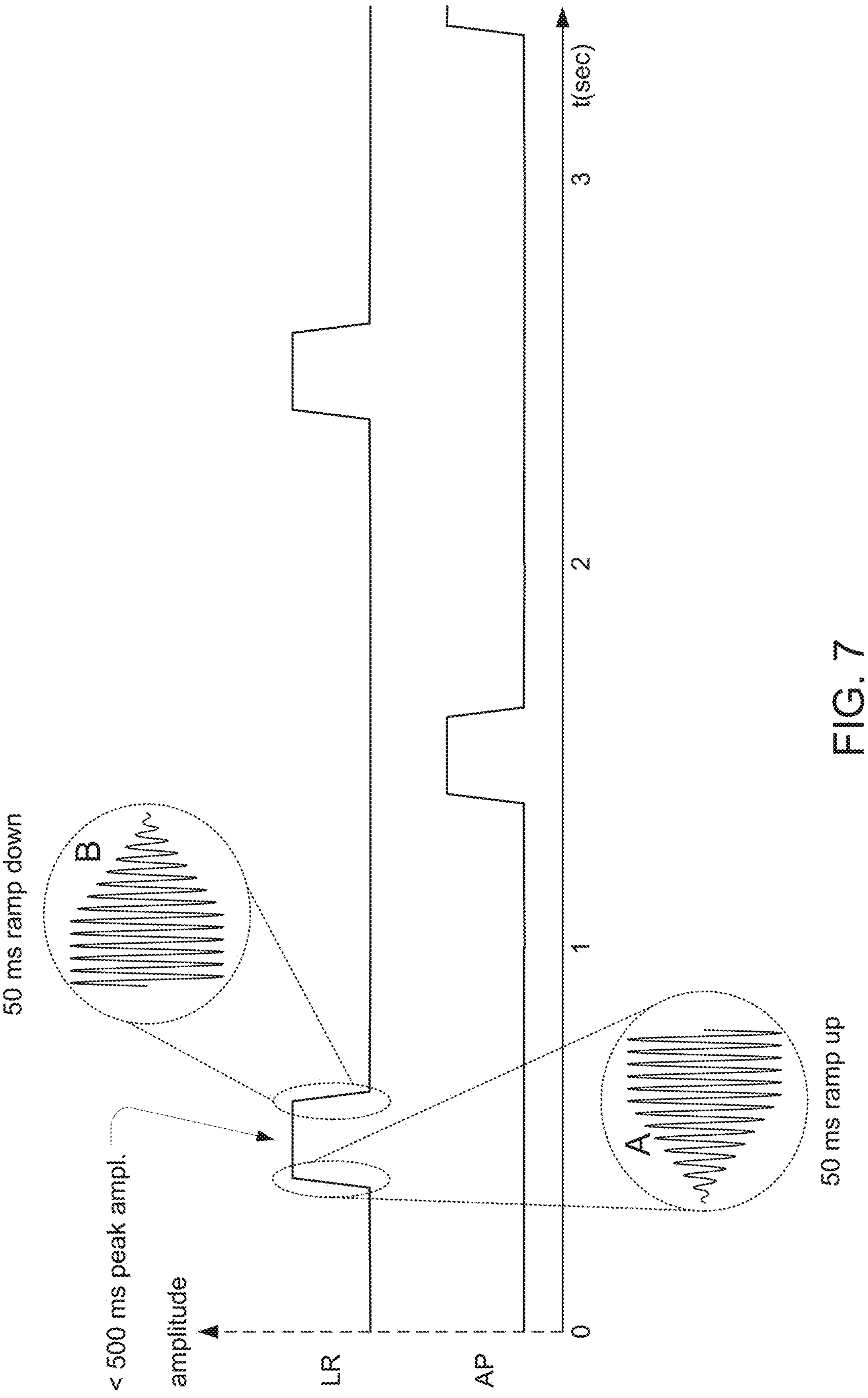
FIG. 7 depicts the AC output amplitudes of the L/R channel and the A/P channel operating in a pulsed mode with short ramp-up and ramp-down times.

For example, the controller 30 can cause the AC signal generator 20 to generate waveforms with the amplitude profile depicted in FIG. 7 by (a) instructing the AC signal generator 20 to remain off for the first 350 ms of each 1 second sub-interval, then (b) instructing the AC signal generator 20 to ramp up its output voltage linearly from zero to a desired peak level in 50 ms by updating the control word once every 1 ms during the next 50 ms; then (c) instructing the AC signal generator 20 to leave its output voltage at the peak level during the next 200 ms; then (d) instructing the AC signal generator 20 to ramp down its output voltage linearly from the peak level to zero in 50 ms by updating the control word once every 1 ms during the next 50 ms; then (e) instructing the AC signal generator 20 to remain off for the last 350 ms of each 1 second sub-interval. Note that the details A and B in FIG. 7 are schematic representations of the instantaneous output voltage during the ramp-up and ramp-down windows. And although each of these details depicts only 9 cycles in the 50 ms ramp-up and ramp-down windows, each of those windows will really contain about 10,000 cycles (assuming 200 kHz TTFields are being delivered).

In other embodiments, the ramp up and ramp down intervals can even be eliminated entirely. For example, the controller 30 can cause the AC signal generator 20 to generate waveforms with the amplitude profile depicted in FIG. 8 by (a) instructing the AC signal generator 20 to remain off for the first 400 ms of each 1 second sub-interval, then (b) instructing the AC signal generator 20 to set its output voltage to the peak level and stay there for the next 200 ms; then (c) instructing the AC signal generator 20 to turn off and remain off for the last 400 ms of each 1 second sub-interval.

Figure 8:
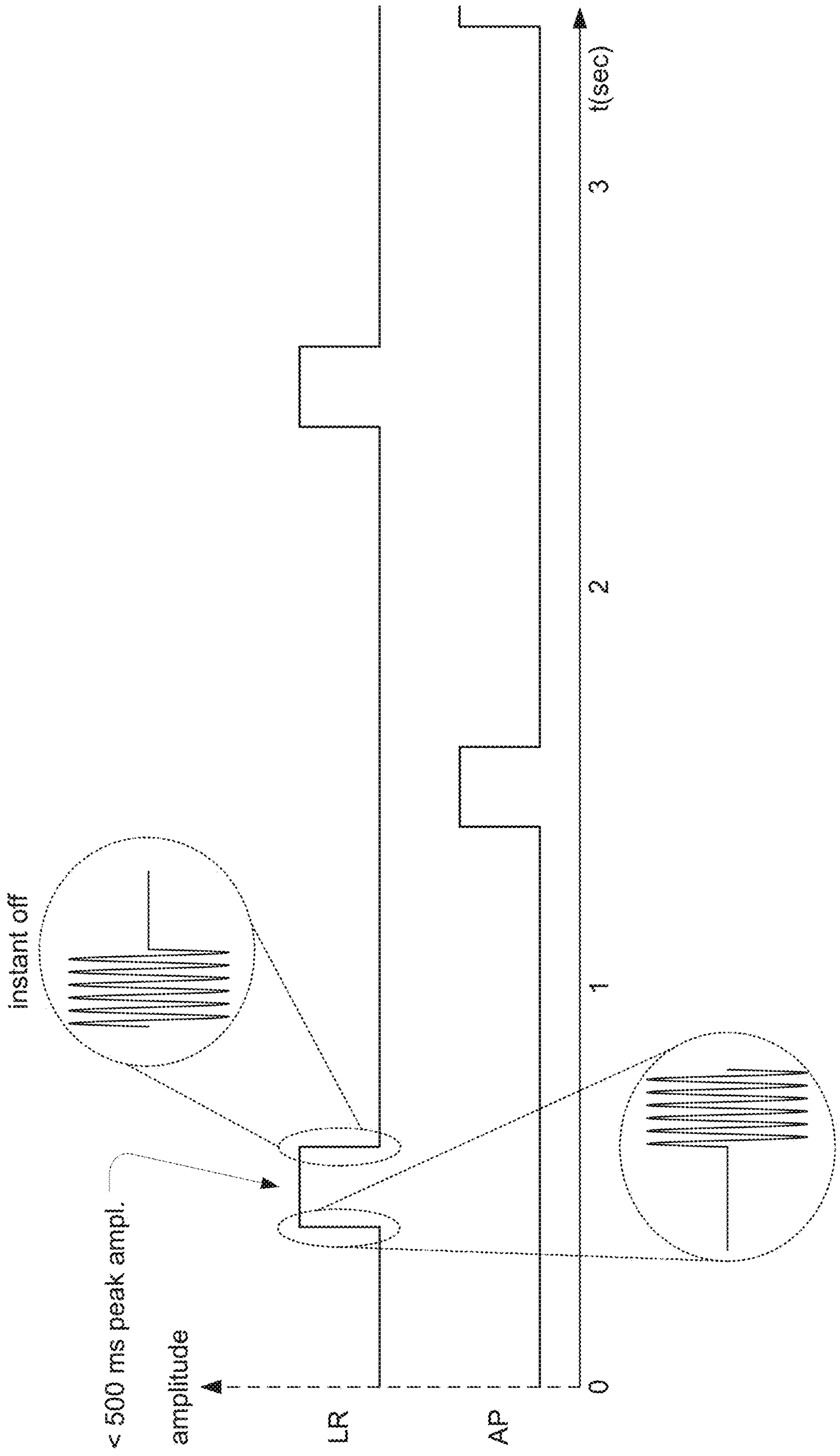
FIG. 8 depicts the AC output amplitudes of the L/R channel and the A/P channel in a pulsed mode when the ramp-up and ramp-down intervals are eliminated entirely.

In the FIGS. 7 and 8 examples, the first and second AC outputs operate at a respective peak amplitude for less than half of each 1 second sub-interval of time (or, in some embodiments, less than 25% of each 1 second sub-interval). In addition, in these examples, the first and second AC outputs remain off at least half the time within each 1 second sub-interval of time (or, in some embodiments, at least 75% of each 1 second sub-interval). And because the output voltages remain off for a large portion of the time, the output voltages can be driven to a higher level for the short time when they are on without overheating. Based on the conclusions described above in connection with FIGS. 5 and 6, the inventors expect the cytotoxicity results for these examples embodiment to be better than the cytotoxicity results that are achieved when the prior art FIG. 1 waveforms are used.

Note that for any given channel (i.e., the L/R channel or the A/P channel) each sub-interval of time during which the AC output voltage remains at its peak for less than half the time does not overlap with the next sub-interval of time during which the AC output voltage remains at its peak for less than half the time. For example, in FIGS. 7 and 8, the sub-interval of time between t=0 and t=1 does not overlap with the sub-interval of time between t=2 and t=3. Similarly, the sub-interval of time between t=1 and t=2 does not overlap with the sub-interval of time between t=3 and t=4.

Note that in some embodiments, including the embodiments depicted in FIGS. 3, 7, and 8, the first and second AC outputs remain within 90% of the respective peak amplitude in each 1 second sub-interval at least 5% of the time.

Additional in vitro experiments were performed on two more cell lines (GL261 and U118) to see how changing various parameters effects cytotoxicity. Parameters that were varied in these experiments include the amount of time the signal was active during each 1 second sub-interval of time, whether ramping up and ramping down was implemented, and the duration of the ramp-up and ramp down times. In these experiments, the direction of the field during any given 1 second sub-interval was switched with respect to the direction that was used during the previous 1 second sub-interval. The duration of each experiment (prior to determining the number of surviving cells) was 72 hours and 120 hours for the GL261 and U118 cell lines, respectively. The results of these experiments are depicted in FIGS. 9-12.

Figure 9:
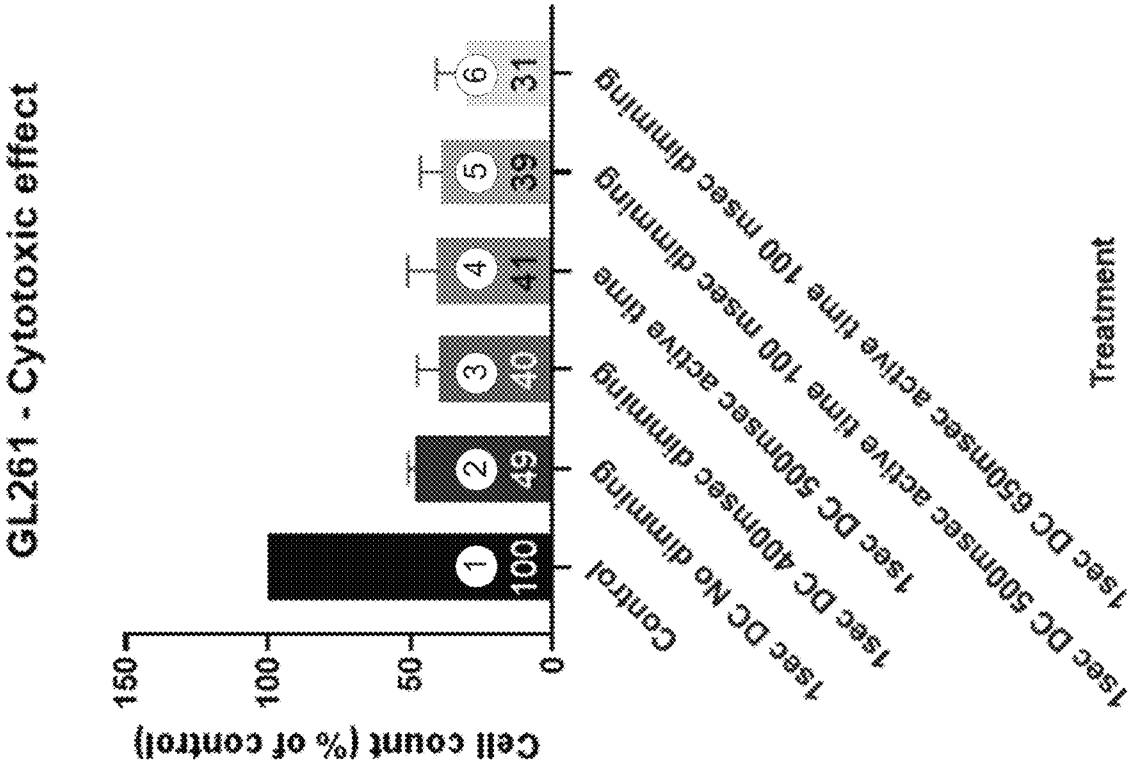
FIG. 9 depicts the results of experiments that were performed to determine how changing various parameters effects cytotoxicity in GL261 cells in vitro.

FIG. 9 depicts the results of these experiments on GL261 cells. The data was obtained using an Inovitro™ system that was modified to provide control over the ramp-up and ramp-down times. Bar #1 represents the control, which was not treated with TTFields. Bar #2 represents the cytotoxicity results when the AC voltage jumped immediately from zero to the peak at the start of each 1 second sub-interval, and jumped immediately from the peak to zero at the end of each 1 second sub-interval. Bar #3 represents the cytotoxicity results when the AC voltage ramped up from zero to the peak in the first 400 ms of each 1 second sub-interval, and ramped down from the peak to zero in the last 400 ms of each 1 second sub-interval. This means that the AC voltage remained at its peak value for 200 ms in each 1 second sub-interval.

Bar #4 represents the cytotoxicity results when the AC voltage was at its peak value for 500 ms during each 1 second sub-interval, and was off for the remainder of each 1 second sub-interval, with instantaneous transitions (i.e., no ramping) between the on and off states. Bar #5 represents the cytotoxicity results when the AC voltage ramped up from zero to the peak in 100 ms, remained at the peak for 300 ms, then ramped down from the peak to zero in 100 ms of each 1 second sub-interval. The AC voltage remained off for the remaining 500 ms of each 1 second sub-interval. Bar #6 represents the cytotoxicity results when the AC voltage ramped up from zero to the peak in 100 ms, remained at the peak for 450 ms, then ramped down from the peak to zero in 100 ms of each 1 second sub-interval. The AC voltage remained off for the remaining 350 ms of each 1 second sub-interval. Notably, the cytotoxicity results for all four cases where the amplitude did not remain at its full value 100% of the time (i.e., bars #3-6) were better than the results when the amplitude remained at its full value 100% of the time (i.e., bar #2).

Figure 10:
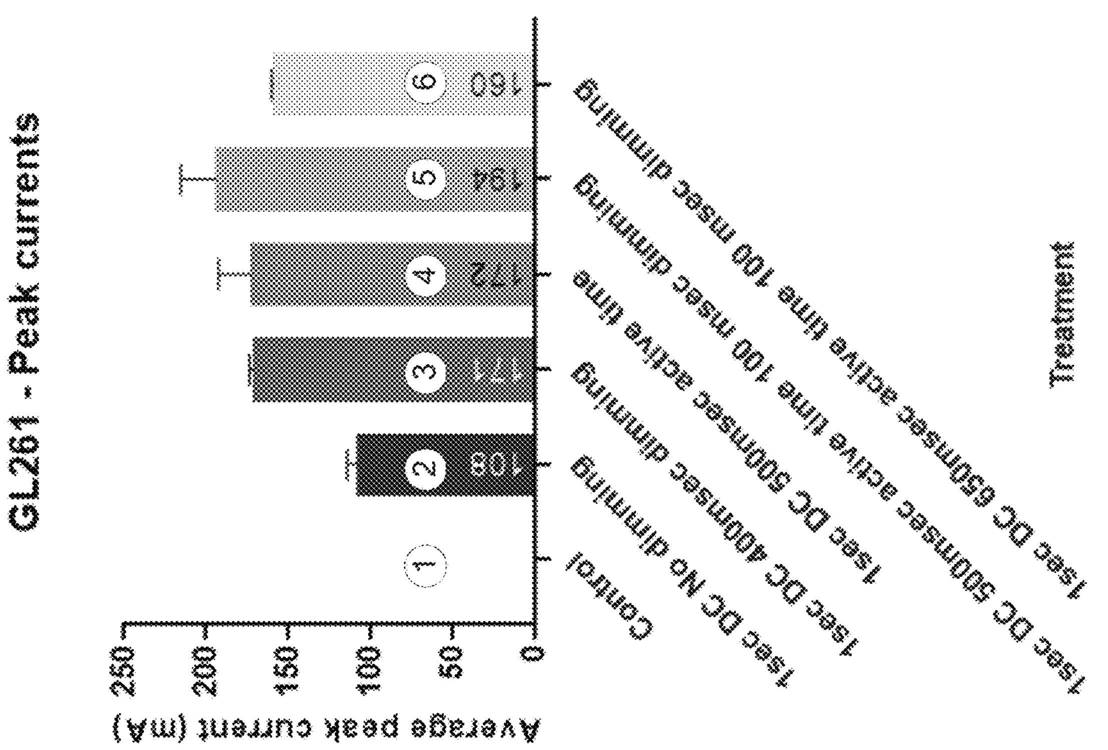
FIG. 10 depicts the peak current that was applied during the FIG. 9 experiments.

FIG. 10 depicts the peak current that was applied by the Inovitro™ system that was modified to provide adjustable ramp-up and ramp-down rates during the FIG. 9 experiments. Each of the numbered bars in FIG. 10 corresponds to a respective numbered bar in FIG. 9.

Figure 11:
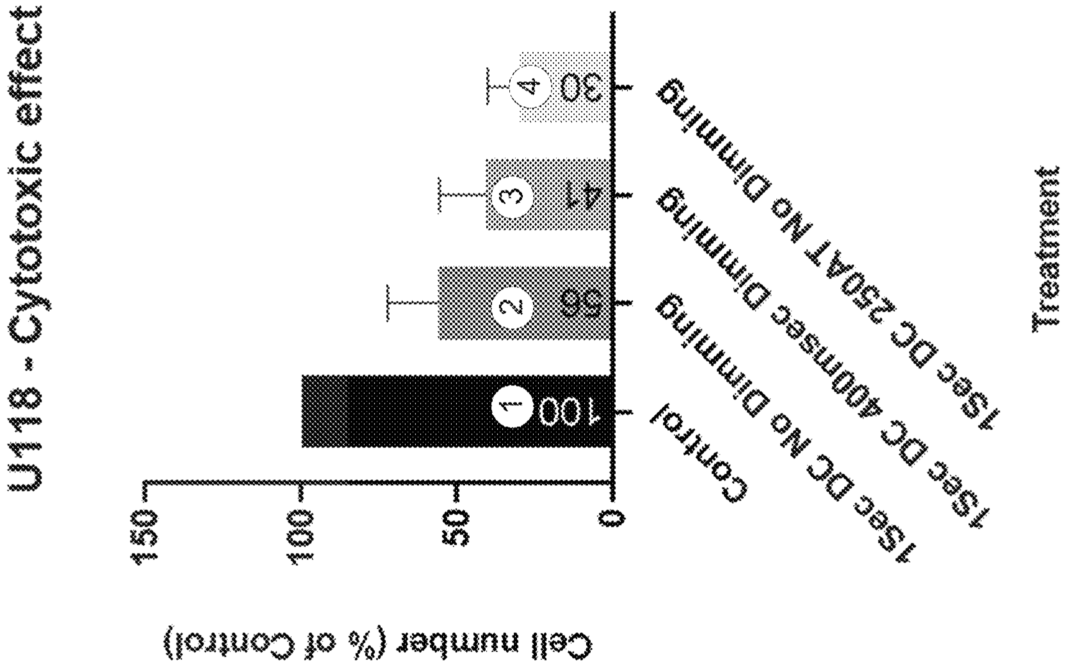
FIG. 11 depicts the results of experiments that were performed to determine how changing various parameters effects cytotoxicity in U118 cells in vitro.

FIG. 11 depicts the results of these experiments on U118 cells. The data was obtained using an Inovitro™ system that was modified to provide control over the ramp-up and ramp-down times. Bar #1 represents the control, which was not treated with TTFields. Bar #2 represents the cytotoxicity results when the AC voltage jumped immediately from zero to the peak at the start of each 1 second sub-interval, and jumped immediately from the peak to zero at the end of each 1 second sub-interval. Bar #3 represents the cytotoxicity results when the AC voltage ramped up from zero to the peak in the first 400 ms of each 1 second sub-interval, and ramped down from the peak to zero in the last 400 ms of each 1 second sub-interval. This means that the AC voltage remained at its peak value for 200 ms in each 1 second sub-interval. Bar #4 represents the cytotoxicity results when the AC voltage was at its peak value for 250 ms during each 1 second sub-interval, and was off for the remainder of each 1 second sub-interval, with instantaneous transitions (i.e., no ramping) between the on and off states. Notably, the cytotoxicity results for both cases where the amplitude did not remain at its full value 100% of the time (i.e., bars #3-4) were better than the results when the amplitude remained at its full value 100% of the time (i.e., bar #2).

Figure 12:
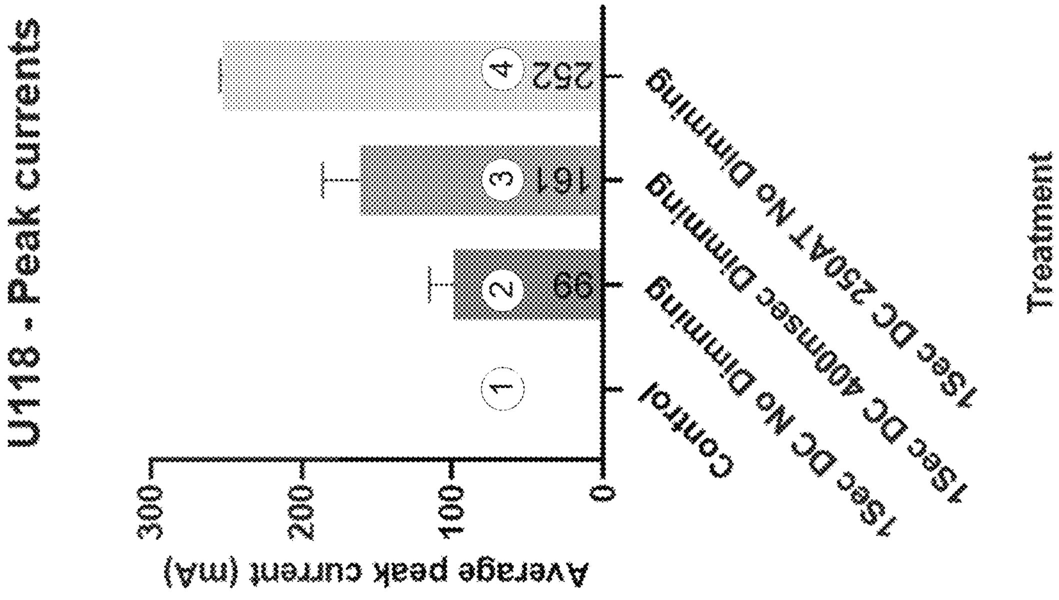
FIG. 12 depicts the peak current that was applied during the FIG. 11 experiments.

FIG. 12 depicts the peak current that was applied by the Inovitro™ system that was modified to provide adjustable ramp-up and ramp-down rates during the FIG. 11 experiments. Each of the numbered bars in FIG. 12 corresponds to a respective numbered bar in FIG. 11.

In the in vitro experiments described above, the frequency of the alternating electric fields was 200 kHz. But in alternative embodiments, the frequency of the alternating electric fields could be another frequency, e.g., about 200 kHz, or between 50 and 500 kHz.

In the in vitro experiments described above, the direction of the alternating electric fields was switched every one second between two perpendicular directions, which means that each sub-interval is 1 second long. But in alternative embodiments, the direction of the alternating electric fields can be switched at a faster rate (e.g., every 1-1000 ms) or at a slower rate (e.g., every 1-360 seconds), in which case the duration of each sub-interval would be shorter or longer than 1 second. Preferably, there are at least 10 sub-intervals per hour, and in some embodiments, there are at least 100 sub-intervals per hour. The duration of treatment is preferably at least 1 hour long, and is more preferably at least 100 or at least 1000 hours long. Optionally, the overall duration of treatment may be interrupted by breaks. For example, applying the alternating fields to a subject for 15 hours per day for 100 days (with a break from treatment each night while the subject sleeps) would result in a total duration of treatment of 1500 hours.

In the in vitro experiments described above, the direction of the alternating electric fields was switched between two perpendicular directions by applying an AC voltage to two pairs of electrodes that are disposed 90° apart from each other in 2D space in an alternating sequence. But in alternative embodiments the direction of the alternating electric fields may be switched between two directions that are not perpendicular by repositioning the pairs of electrodes, or between three or more directions (assuming that additional pairs of electrodes are provided). For example, the direction of the alternating electric fields may be switched between three directions, each of which is determined by the placement of its own pair of electrodes. Optionally, these three pairs of electrodes may be positioned so that the resulting fields are disposed 90° apart from each other in 3D space. In other alternative embodiments, the electrodes need not be arranged in pairs. See, for example, the electrode positioning described in U.S. Pat. No. 7,565,205, which is incorporated herein by reference. In other alternative embodiments, the direction of the field remains constant, (in which case the AC signal generator 20 can have only a single output).

In the in vitro experiments described above, the electrical field was capacitively coupled into the culture because the modified Inovitro™ system used conductive electrodes disposed on the outer surface of the dish sidewalls, and the ceramic material of the sidewalls acts as a dielectric. But in alternative embodiments, the electric field could be applied directly to the cells without capacitive coupling (e.g., by modifying the Inovitro™ system configuration so that the conductive electrodes are disposed on the sidewall's inner surface instead of on the sidewall's outer surface).

The methods described herein can also be applied in the in vivo context by applying the alternating electric fields to a target region of a live subject's body, for both glioblastoma cells and other types of cancer cells. This may be accomplished, for example, by positioning electrodes on or below the subject's skin so that application of an AC voltage between selected subsets of those electrodes will impose the alternating electric fields in the target region of the subject's body.

For example, in situations where the relevant cells are located in the subject's lungs, one pair of electrodes could be positioned on the front and back of the subject's thorax, and a second pair of electrodes could be positioned on the right and left sides of the subject's thorax. In some embodiments, the electrodes are capacitively coupled to the subject's body (e.g., by using electrodes that include a conductive plate and also have a dielectric layer disposed between the conductive plate and the subject's body). But in alternative embodiments, the dielectric layer may be omitted, in which case the conductive plates would make direct contact with the subject's body. In another embodiment, electrodes could be inserted subcutaneously below a patient's skin. An AC voltage generator applies an AC voltage at a selected frequency (e.g., 200 kHz) between the right and left electrodes for a first period of time (e.g. 1 second), which induces alternating electric fields where the most significant components of the field lines are parallel to the transverse axis of the subject's body. Then, the AC voltage generator applies an AC voltage at the same frequency (or a different frequency) between the front and back electrodes for a second period of time (e.g. 1 second), which induces alternating electric fields where the most significant components of the field lines are parallel to the sagittal axis of the subject's body. This two step sequence is then repeated for the duration of the treatment. Optionally, thermal sensors may be included at the electrodes, and the AC voltage generator can be configured to decrease the amplitude of the AC voltages that are applied to the electrodes if the sensed temperature at the electrodes gets too high. In some embodiments, one or more additional pairs of electrodes may be added and included in the sequence. In alternative embodiments, only a single pair of electrodes is used, in which case the direction of the field lines is not switched. Note that any of the parameters for this in vivo embodiment (e.g., frequency, field strength, duration, direction-switching rate, and the placement of the electrodes) may be varied as described above in connection with the in the vitro embodiments. But care must be taken in the in vivo context to ensure that the electric field remains safe for the subject at all times.

In the examples described above, the ramp up and ramp down intervals match. But in alternative embodiments and instances, those two intervals could be different. For example, the ramp up time could be 100 ms, and the ramp down time could be 50 ms. Or the ramp up time could be 100 ms, and the ramp down time could be eliminated entirely.

In the examples described above, the timing of the signals that are applied to the L/R electrodes matches the timing of the signals that are applied to the A/P electrodes. But in alternative embodiments and instances, the timing of those two signals could be different. For example, the signal applied to the L/R electrodes could be active for 500 ms out of each 1 second sub-interval, while the signal applied to the A/P electrodes could be active for 300 ms out of each 1 second sub-interval.

By using the methods and apparatuses described herein, the growth of cancer cells can be inhibited, with improved inhibition of growth with respect to the prior art.

In the embodiments described above, in each of the sub-intervals of time, (a) the alternating electric field has a frequency between 50 and 500 kHz, (b) the alternating electric field has a respective peak intensity of at least 1 V/cm in at least a portion of the cancer cells, and (c) the alternating electric field remains at the respective peak intensity less than half the time. But in alternative embodiments, those parameters can be relaxed to some extent so that (a) the alternating electric field has a frequency between 50 kHz and 1 MHz, (b) the alternating electric field has a respective peak intensity of at least 0.1 V/cm in at least a portion of the cancer cells, and (c) the alternating electric field remains at the respective peak intensity less than 75% of the time.

Thus, another aspect of the invention is directed to a second method of inhibiting growth of cancer cells. The second method comprises applying an alternating electric field to the cancer cells during a first interval of time that is at least 1 hour long, wherein the first interval of time includes a plurality of non-overlapping sub-intervals of time per hour. In each of the sub-intervals of time, (a) the alternating electric field has a frequency between 50 kHz and 1 MHz, (b) the alternating electric field has a respective peak intensity of at least 0.1 V/cm in at least a portion of the cancer cells, and (c) the alternating electric field remains at the respective peak intensity less than 75% of the time.

In some instances of the second method, within each of the sub-intervals of time, the alternating electric field ramps up to the respective peak intensity during an interval of time that precedes the respective peak intensity. Optionally, in these instances, within each of the sub-intervals of time, the alternating electric field ramps up linearly to the respective peak intensity during the interval of time that precedes the respective peak intensity.

In some instances of the second method, within each of the sub-intervals of time, the alternating electric field remains off at least 75% of the time.

In some instances of the second method, within each of the sub-intervals of time, the alternating electric field remains at the respective peak intensity less than 25% of the time. Optionally, in these instances, within each of the sub-intervals of time, the alternating electric field remains off at least 75% of the time. Optionally, in these instances, within each of the sub-intervals of time, the alternating electric field remains within 90% of the respective peak intensity at least 5% of the time.

In some instances of the second method, within each of the sub-intervals of time, the alternating electric field has a respective peak intensity of 1-10 V/cm in at least a portion of the cancer cells.

In some instances of the second method, the first interval of time includes at least 3, for example at least 10 non-overlapping sub-intervals of time per hour. In some instances of the second method, the alternating electric field is applied to the cancer cells in a first direction during a first subset of the sub-intervals, and the alternating electric field is applied to the cancer cells in a second direction during a second subset of the sub-intervals, wherein the second direction is offset from the first direction by at least 45°.

In some instances of the second method, within each of the sub-intervals of time, the alternating electric field remains at the respective peak intensity less than 25% of the time; the first interval of time includes at least 3, for example at least 10 non-overlapping sub-intervals of time per hour; the alternating electric field is applied to the cancer cells in a first direction during a first subset of the sub-intervals; and the alternating electric field is applied to the cancer cells in a second direction during a second subset of the sub-intervals, wherein the second direction is offset from the first direction by at least 45°.

Similarly, another aspect of the invention is directed to a second apparatus that comprises a signal generator and a controller. The signal generator has at least one control input, and the signal generator is configured to generate a first AC output at a frequency between 50 kHz and 1 MHz. The first AC output has an amplitude that depends on a state of the at least one control input. The controller is configured to send a first set of control signals to the at least one control input during each of a plurality of non-overlapping first sub-intervals of time per hour, and the first set of control signals is configured to cause the first AC output to operate at a respective peak amplitude for less than 75% of each respective first sub-interval of time.

In some embodiments of the second apparatus, the first set of control signals is configured so that during each of the first sub-intervals of time, the first set of control signals will cause the first AC output to ramp up to the respective peak amplitude during an interval of time that precedes the respective peak amplitude. Optionally, in these embodiments, the first set of control signals is configured so that during each of the first sub-intervals of time, the first set of control signals will cause the first AC output to ramp up linearly to the respective peak amplitude during the interval of time that precedes the respective peak amplitude.

In some embodiments of the second apparatus, the first set of control signals is configured so that during each of the first sub-intervals of time, the first set of control signals will cause the first AC output to remain off at least 75% of the time.

In some embodiments of the second apparatus, the first set of control signals is configured so that during each of the first sub-intervals of time, the first set of control signals will cause the first AC output to remain at the respective peak amplitude less than 25% of the time.

Optionally, in the embodiments of the previous paragraph, the first set of control signals is configured so that during each of the first sub-intervals of time, the first set of control signals will cause the first AC output to remain off at least 75% of the time.

Optionally, in the embodiments of the previous paragraph, the first set of control signals is configured so that during each of the first sub-intervals of time, the first set of control signals will cause the first AC output to remain within 90% of the respective peak amplitude at least 5% of the time.

In some embodiments of the second apparatus, the first set of control signals is configured so that during each of the first sub-intervals of time, the first set of control signals will cause the first AC output to have a respective peak amplitude of at least 50 V.

In some embodiments of the second apparatus, the controller is configured to send the first set of control signals to the at least one control input during each of at least 10 non-overlapping first sub-intervals of time per hour.

In some embodiments of the second apparatus, the signal generator is further configured to generate a second AC output at a frequency between 50 kHz and 1 MHz; the second AC output has an amplitude that depends on a state of the at least one control input; and the controller is further configured to send a second set of control signals to the at least one control input during each of a plurality of non-overlapping second sub-intervals of time per hour, wherein the second set of control signals is configured to cause the second AC output to operate at a respective peak amplitude for less than 75% of each second respective sub-interval of time, and wherein each of the second sub-intervals of time follows a respective one of the first sub-intervals of time.

Optionally, in the embodiments of the previous paragraph, the first set of control signals is configured so that during each of the first sub-intervals of time, the first set of control signals will cause the first AC output to remain at the respective peak amplitude less than 25% of the time, and the second set of control signals is configured so that during each of the second sub-intervals of time, the second set of control signals will cause the second AC output to remain at the respective peak amplitude less than 25% of the time.

Optionally, in the embodiments of the previous paragraph, the controller is configured to send the first set of control signals to the at least one control input during each of at least 10 non-overlapping first sub-intervals of time per hour, and the controller is configured to send the second set of control signals to the at least one control input during each of at least 10 non-overlapping second sub-intervals of time per hour.

Optionally, in the embodiments of the previous paragraph, the first set of control signals is configured so that during each of the first sub-intervals of time, the first set of control signals will cause the first AC output to have a respective peak amplitude of at least 50 V, and the second set of control signals is configured so that during each of the second sub-intervals of time, the second set of control signals will cause the second AC output to have a respective peak amplitude of at least 50 V.

Although the discussion above is presented in the context of applying alternating electric fields to cancer cells in vitro and/or in vivo, the same concepts can be used when applying alternating electric fields to a subject's body for other purposes, including but not limited to increasing the permeability of the blood brain barrier and increasing the permeability of cell membranes, as described in U.S. Pat. Nos. 10,967,167 and 11,103,698, each of which is incorporated herein by reference in its entirety.

In these contexts, a third method of applying electric fields to a target region in a living body may be used. The third method comprises applying an alternating electric field to the target region during a first interval of time that is at least 1 hour long, wherein the first interval of time includes a plurality of non-overlapping sub-intervals of time per hour. In each of the sub-intervals of time, (a) the alternating electric field has a frequency between 50 kHz and 1 MHz, (b) the alternating electric field has a respective peak intensity of at least 0.1 V/cm in at least a portion of the target region, and (c) the alternating electric field remains at the respective peak intensity less than 75% the time.

In some instances of the third method, within each of the sub-intervals of time, the alternating electric field ramps up to the respective peak intensity during an interval of time that precedes the respective peak intensity. Optionally, in these instances, within each of the sub-intervals of time, the alternating electric field ramps up linearly to the respective peak intensity during the interval of time that precedes the respective peak intensity.

In some instances of the third method, within each of the sub-intervals of time, the alternating electric field remains off at least 75% of the time.

In some instances of the third method, within each of the sub-intervals of time, the alternating electric field remains at the respective peak intensity less than 50%, for example less than 25% of the time. Optionally, in these instances, within each of the sub-intervals of time, the alternating electric field remains off at least 75% of the time. Optionally, in these instances, within each of the sub-intervals of time, the alternating electric field remains within 90% of the respective peak intensity at least 5% of the time.

In some instances of the third method, within each of the sub-intervals of time, the alternating electric field has a respective peak intensity of 1-10 V/cm in at least a portion of the target region.

In some instances of the third method, the first interval of time includes at least 10 non-overlapping sub-intervals of time per hour. In some instances of the third method, the alternating electric field is applied to the target region in a first direction during a first subset of the sub-intervals, and the alternating electric field is applied to the target region in a second direction during a second subset of the sub-intervals, wherein the second direction is offset from the first direction by at least 45°.

In some instances of the third method, within each of the sub-intervals of time, the alternating electric field remains at the respective peak intensity less than half the time; the first interval of time includes at least 10 non-overlapping sub-intervals of time per hour; the alternating electric field is applied to the target region in a first direction during a first subset of the sub-intervals; and the alternating electric field is applied to the target region in a second direction during a second subset of the sub-intervals, wherein the second direction is offset from the first direction by at least 45°.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus comprising:

a signal generator having at least one control input, wherein the signal generator is configured to generate a first AC output at a frequency between 50 and 500 kHz and a second AC output at a frequency between 50 and 500 kHz, wherein the first AC output has an amplitude that depends on a state of the at least one control input, and wherein the second AC output has an amplitude that depends on a state of the at least one control input; and a controller configured to send a first set of control signals to the at least one control input during each of a plurality of non-overlapping first sub-intervals of time per hour, wherein the first set of control signals is configured to cause the first AC output to operate at a respective peak amplitude for less than half of each respective first sub-interval of time, wherein the controller is further configured to send a second set of control signals to the at least one control input during each of a plurality of non-overlapping second sub-intervals of time per hour, and wherein the second set of control signals is configured to cause the second AC output to operate at a respective peak amplitude for less than half of each respective second sub-interval of time, wherein each of the second sub-intervals of time (a) follows a respective one of the first sub-intervals of time and (b) does not overlap with the respective one of the first sub-intervals of time.

2. The apparatus of claim 1, wherein the first set of control signals is configured so that during each of the first sub-intervals of time, the first set of control signals will cause the first AC output to ramp up to the respective peak amplitude during an interval of time that precedes the respective peak amplitude.

3. The apparatus of claim 1, wherein the first set of control signals is configured so that during each of the first sub-intervals of time, the first set of control signals will cause the first AC output to remain off at least half the time.

4. The apparatus of claim 1, wherein the first set of control signals is configured so that during each of the first sub-intervals of time, the first set of control signals will cause the first AC output to remain at the respective peak amplitude less than 25% of the time.

5. The apparatus of claim 1, wherein the first set of control signals is configured so that during each of the first sub-intervals of time, the first set of control signals will cause the first AC output to remain off at least 75% of the time.

6. The apparatus of claim 4, wherein the first set of control signals is configured so that during each of the first sub-intervals of time, the first set of control signals will cause the first AC output to remain within 90% of the respective peak amplitude at least 5% of the time.

7. The apparatus of claim 1, wherein the controller is configured to send the first set of control signals to the at least one control input during each of at least 10 non-overlapping first sub-intervals of time per hour, and wherein the controller is configured to send the second set of control signals to the at least one control input during each of at least 10 non-overlapping second sub-intervals of time per hour.

8. The apparatus of claim 1, wherein the first set of control signals is configured so that during each of the first sub-intervals of time, the first set of control signals will cause the first AC output to remain at the respective peak amplitude less than 25% of the time and wherein the second set of control signals is configured so that during each of the second sub-intervals of time, the second set of control signals will cause the second AC output to remain at the respective peak amplitude less than 25% of the time.

9. The apparatus of claim 8, wherein the controller is configured to send the first set of control signals to the at least one control input during each of at least 10 non-overlapping first sub-intervals of time per hour, and wherein the controller is configured to send the second set of control signals to the at least one control input during each of at least 10 non-overlapping second sub-intervals of time per hour.

10. The apparatus of claim 1, wherein each of the first sub-intervals of time has a duration between 1 and 360 seconds, and wherein each of the second sub-intervals of time has a duration between 1 and 360 seconds.

11. The apparatus of claim 1, wherein each of the first sub-intervals of time has a duration of at least 1 second, and wherein each of the second sub-intervals of time has a duration of at least 1 second.

12. An apparatus comprising:

a signal generator having at least one control input, wherein the signal generator is configured to generate a first AC output at a frequency between 50 and 500 kHz and a second AC output at a frequency between 50 and 500 kHz, wherein the first AC output has an amplitude that depends on a state of the at least one control input, and wherein the second AC output has an amplitude that depends on a state of the at least one control input; and a controller configured to send a first set of control signals to the at least one control input during each of a plurality of non-overlapping first sub-intervals of time per hour, wherein the first set of control signals is configured to cause the first AC output to operate at a respective peak amplitude for 20-30% of each respective first sub-interval of time, wherein the controller is further configured to send a second set of control signals to the at least one control input during each of a plurality of non-overlapping second sub-intervals of time per hour, and wherein the second set of control signals is configured to cause the second AC output to operate at a respective peak amplitude for 20-30% of each respective second sub-interval of time, and wherein each of the second sub-intervals of time (a) follows a respective one of the first sub-intervals of time and (b) does not overlap with the respective one of the first sub-intervals of time.

13. The apparatus of claim 12, wherein the first set of control signals is configured so that during each of the first sub-intervals of time, the first set of control signals will cause the first AC output to ramp up to the respective peak amplitude during an interval of time that precedes the respective peak amplitude, and wherein the second set of control signals is configured so that during each of the second sub-intervals of time, the second set of control signals will cause the second AC output to ramp up to the respective peak amplitude during an interval of time that precedes the respective peak amplitude.

14. The apparatus of claim 12, wherein the first set of control signals is configured so that during each of the first sub-intervals of time, the first set of control signals will cause the first AC output to remain within 90% of the respective peak amplitude at least 5% of the time, and wherein the second set of control signals is configured so that during each of the second sub-intervals of time, the second set of control signals will cause the second AC output to remain within 90% of the respective peak amplitude at least 5% of the time.

15. The apparatus of claim 12, wherein the controller is configured to send the first set of control signals to the at least one control input during each of at least 10 non-overlapping first sub-intervals of time per hour, and wherein the controller is configured to send the second set of control signals to the at least one control input during each of at least 10 non-overlapping second sub-intervals of time per hour.

16. The apparatus of claim 12, wherein each of the first sub-intervals of time has a duration between 1 and 360 seconds, and wherein each of the second sub-intervals of time has a duration between 1 and 360 seconds.

17. The apparatus of claim 12, wherein each of the first sub-intervals of time has a duration of at least 1 second, and wherein each of the second sub-intervals of time has a duration of at least 1 second.

18. An apparatus comprising:

a signal generator having at least one control input, wherein the signal generator is configured to generate a first AC output at a frequency between 50 and 500 kHz and a second AC output at a frequency between 50 and 500 kHz, wherein the first AC output has an amplitude that depends on a state of the at least one control input, and wherein the second AC output has an amplitude that depends on a state of the at least one control input; and a controller configured to send a first set of control signals to the at least one control input during each of a plurality of non-overlapping first sub-intervals of time per hour, wherein the first set of control signals is configured to cause the first AC output to operate at a respective peak amplitude for less than half of each respective first sub-interval of time, wherein the controller is further configured to send a second set of control signals to the at least one control input during each of a plurality of non-overlapping second sub-intervals of time per hour, and wherein the second set of control signals is configured to cause the second AC output to operate at a respective peak amplitude for less than half of each respective second sub-interval of time, wherein each of the second sub-intervals of time (a) follows a respective one of the first sub-intervals of time and (b) does not overlap with the respective one of the first sub-intervals of time, wherein the first set of control signals is configured so that during each of the first sub-intervals of time, the first set of control signals will cause the first AC output to remain off at least half the time, and wherein the second set of control signals is configured so that during each of the second sub-intervals of time, the second set of control signals will cause the second AC output to remain off at least half the time.

19. The apparatus of claim 18, wherein the first set of control signals is configured so that during each of the first sub-intervals of time, the first set of control signals will cause the first AC output to remain off at least 75% of the time, and wherein the second set of control signals is configured so that during each of the second sub-intervals of time, the second set of control signals will cause the second AC output to remain off at least 75% of the time.

20. The apparatus of claim 18, wherein the first set of control signals is configured so that during each of the first sub-intervals of time, the first set of control signals will cause the first AC output to remain within 90% of the respective peak amplitude at least 5% of the time, and wherein the second set of control signals is configured so that during each of the second sub-intervals of time, the second set of control signals will cause the second AC output to remain within 90% of the respective peak amplitude at least 5% of the time.

21. The apparatus of claim 18, wherein the controller is configured to send the first set of control signals to the at least one control input during each of at least 10 non-overlapping first sub-intervals of time per hour, and wherein the controller is configured to send the second set of control signals to the at least one control input during each of at least 10 non-overlapping second sub-intervals of time per hour.

22. The apparatus of claim 18, wherein each of the first sub-intervals of time has a duration between 1 and 360 seconds, and wherein each of the second sub-intervals of time has a duration between 1 and 360 seconds.

23. The apparatus of claim 18, wherein each of the first sub-intervals of time has a duration of at least 1 second, and wherein each of the second sub-intervals of time has a duration of at least 1 second.

* * * * *